United States Patent
Llop

(10) Patent No.: US 9,004,919 B2
(45) Date of Patent: Apr. 14, 2015

(54) APPARATUS AND DIGITAL METHOD FOR PREPARATION OF A FOR THE PROMOTION OF A DESIRED EMERGENT SULCUS

(76) Inventor: Daniel R. Llop, Reno, NV (US)

( * ) Notice: Subject to any disclaimer, the term of this patent is extended or adjusted under 35 U.S.C. 154(b) by 264 days.

(21) Appl. No.: 13/176,715

(22) Filed: Jul. 5, 2011

(65) Prior Publication Data

US 2012/0003610 A1 Jan. 5, 2012

Related U.S. Application Data

(60) Provisional application No. 61/361,287, filed on Jul. 2, 2010.

(51) Int. Cl.
*A61C 1/00* (2006.01)
*A61C 1/08* (2006.01)

(52) U.S. Cl.
CPC ...................................... *A61C 1/084* (2013.01)

(58) Field of Classification Search
CPC ...................................... A61C 1/084
USPC .............. 433/172, 173, 174, 175, 201.1, 213; 700/98

See application file for complete search history.

(56) References Cited

U.S. PATENT DOCUMENTS

2010/0105011 A1* 4/2010 Karkar et al. ................. 433/215

FOREIGN PATENT DOCUMENTS

WO PCT/US201/042983 1/2013

OTHER PUBLICATIONS

PCT International Search Report for PCT/US20111042983.

* cited by examiner

*Primary Examiner* — Ralph Lewis
(74) *Attorney, Agent, or Firm* — John D. Long, Esq.; Long & Chybik

(57) ABSTRACT

One possible embodiment of the invention could be a methodology of creating a proposed sulcus emergence profile for a dental implant surgical site, comprising of the following steps obtaining data of a specific patient's mouth needed to create a computer-generated virtual model of that patient's mouth; processing said obtained data to create a computer-generated virtual model of the patient's mouth; comparing virtual model data as it pertains to a site map of a proposed dental implant surgical site with virtual model data as it pertains to a site map of a mirror location in the mouth of the surgical site, allowing the mirror location site map to be transposed and overlaid upon the site map of the surgical site; and creating from that comparison of virtual model data, a proposed sulcus emergence profile for the implant surgical site.

21 Claims, 4 Drawing Sheets

APPARATUS AND DIGITAL METHOD FOR PREPARATION OF A FOR THE PROMOTION OF A DESIRED EMERGENT SULCUS

CROSS-REFERENCES TO RELATED APPLICATIONS

This application claims the benefit under 35 U.S.C. §119(e) of U.S. Provisional Patent Application No. 61/361,287, filed on Jul. 2, 2010, the contents of which are relied upon and incorporated by reference.

STATEMENT REGARDING FEDERALLY SPONSORED RESEARCH OR DEVELOPMENT

Not Applicable

REFERENCE TO A "MICROFICHE APPENDIX"

Not Applicable.

FIELD OF THE INVENTION

The present invention generally relates to dental digital methodologies used in creating patient-specific map of the mouth. More particularity to those dental digital methodologies for using such maps in determining and bring about the optimization of a desired real life profile of the emergent sulcus of a removed tooth utilizing dental implant technology.

BACKGROUND

As a person continues to age, tooth loss inevitably occurs, and tooth replacement, as provided by the dental profession, is often employed to make up for the tooth loss. One of the more important aspects of this replacement procedure is that the sulcus (e.g., soft tissue complex as impacted by hard tissue/bone structure of the mouth) as attached to the cortical occlusal bone and provides the free gingival margin (e.g. the gum line surrounding the [now lost] tooth or the replacement crown) changes once the natural tooth is removed. In some cases, the bone portion (or hard tissue) of the mouth where the tooth was formerly anchored, can, through the normal healing process, compact upon itself and as result change the bone line while gum tissue from that portion of mouth can also recede or become thinner thus changing the overall profile of cortical plate or jaw shape at that point. These changes may make the establishment of an implant surgical site (with corresponding, eventual placement of a dental crown upon a dental implant at the implant surgical site) more difficult, especially in those areas such as the front of the mouth where the bone and tissue are much thinner structures with corresponding less material to anchor the dental implant. This change in profile may result in a limitation of the needed telemetry and other implant orientations for proper implant placement and anchorage, and well as, unless otherwise corrected, ultimately place the dental crown in a position within the mouth that would appear to be out of alignment or otherwise appear to be in an unnatural placement in relation to the surrounding teeth. The new crown may properly support the bite of the patient but appear to have an unnatural orientation, calling attention to the crown, thus defeating one of the cosmetic purposes of tooth replacement: that persons observing the patient's smile should not notice the occurrence of dental implant/tooth replacement.

What dentistry has attempted in the past is use a healing abutment to manually rectify these changes in bone and sulcus and improve the operation site for the placement of the implant. Such healing abutments in manufacture generally have a circular lateral cross section, substantially generic in construction; and generally do not provide a profile that is patient-specific, or much less tooth-specific, for proper growth of a desired sulcus profile that could match the base of the dental crown, match the overall presentation of the remaining teeth, in a manner that is both healthy and elastically pleasing.

In operation, after the soft tissue is cut and removed to designate implant surgical site, the dental implant is secured to the implant surgical site, the bottom of the implant being embedded into the bone. A healing abutment is then attached to the exposed top portion of the dental implant. Once the tissue healing (and bone solidification/osseointegration around the buried/artificial root portion of the implant) has finalized, the healing abutment is replaced with a final abutment, with the healing abutment being discarded. Procedures are then utilized as needed to place and permanently secure the dental crown to the healing abutment/dental implant combination.

However, if the sulcus did not heal properly or grew away from the dental implant and does not provide an appropriate free gingival margin (e.g., gum line) and the like, further surgical procedures may be implemented to manually sculpt the soft tissue (and possibly bone) as required to generally bring the sulcus into a proper orientation and required contact with the placed dental crown. These post operative procedures are costly, painful, as well as time-consuming.

What is needed therefore is a pre-surgical digital method or process and associated apparatus wherein computer virtual modeling utilizes and merges DICOM data sets taken from the patient's mouth such as a CBCT scan (for the bone structure, root trajectory, and alike); optical scan data; scanned physical impressions/castings (for tissue structure); digital impression, and the like to create pre-dental implant surgery, a virtual model of what the desired emergent sulcus for the proposed implant site should be. Utilizing this digital data prior to implant surgery, a temporary (e.g., disposable) healing abutment can be virtually designed to meet a desired emergent sulcus profile. By virtually placing such a healing abutment upon a virtual implant body at a virtual implant operation site, the dimensions of the healing abutment can be checked to see that when the healing abutment is actually placed at the surgical implant site that it could properly support the development of the projected desired emergent sulcus profile; when the final abutment is actually placed at the surgical implant site that it could properly support emergent sulcus profile as predicted; when emergent sulcus profile is obtained that could not only properly accommodate the placed crown. In this manner, the overall combination of the developed emergent sulcus, implant, healing abutment, and crown could also substantially match the patient's natural overall sulcus profile and gingival harmony.

SUMMARY OF ONE EMBODIMENT OF THE INVENTION

Advantages of One or More Embodiments of the Present Invention

The various embodiments of the present invention may, but do not necessarily, achieve one or more of the following advantages:

to provide a computer-generated virtual model of the patient's mouth to compare the implant surgical site with it's mirror site/location on the contra-lateral side of the patient's mouth to create a emerging sulcus profile for a implant surgical site that would be biologically correct and esthetically pleasing when a dental crown is finally fitted to the operation surgical site;

to provide a virtual model of a mouth that is a patient-specific, biologically correct shape and position for an implant surgical site that consequently gives the dental healthcare profession the ability to plan (e.g., pre-operatively and virtually) the profile emergent sulcus to create a concavity or tooth socket for implant surgery;

the ability to use virtual mapping and modeling (e.g., Rapid Prototyped CAD/CAM) to manufacture a temporary, patient-specific healing abutment designed to promote a specific profile of an emergent sulcus at an implant surgical site;

to provide a specifically engineered patient-specific healing abutment at a implant surgical to assist the promotion of desired emergent sulcus abutment;

the ability to utilize the patient-specific healing abutment dimensions to further design and manufacture a final abutment upon which that the final crown will be permanently affixed, the base of final abutment and the base of the crown matching the desired emergent sulcus profile; and the pre-surgical ability to establish a profile of an emergent sulcus for a proposed dental implant site and to use the profile to manufacture a healing abutment (and manufacture a final abutment and crown utilizing many of the healing abutment's dimensions) designed to bring about the desired emergent sulcus once attached to the implant surgical site.

These and other advantages may be realized by reference to the remaining portions of the specification, claims, and abstract.

Brief Description of One Embodiment of the Present Invention

One possible embodiment of the invention could be method of creating a proposed sulcus emergent profile for a dental implant surgical site, comprising of the following steps, but not necessarily in the order shown: below obtaining data of a specific patient's mouth needed to create a computer-generated virtual model of that patient's mouth; processing said obtained data to create a computer-generated virtual model of the specific patient's mouth; comparing virtual model data as it pertains to a site map of a proposed dental implant surgical site of the patient's mouth with other virtual model data as it pertains to a site map of the mirror location of surgical site, allowing the site map of the mirror location to be transposed and overlaid upon the site map of proposed dental implant surgical site; and creating from that comparison of virtual model data, a proposed sulcus emergent profile for the implant surgical site.

One possible embodiment of the invention could be a method or process of creating a patient-specific healing abutment that meets a proposed sulcus emergent profile for a dental implant surgical site, comprising of the following steps, obtaining data of a specific patient's mouth needed to create a computer-generated virtual model of that patient's mouth; processing said obtained data to create a computer-generated virtual model of the current state of the specific patient's mouth; comparing data of virtual model as it pertains to a site map of a proposed dental implant surgical site of the patient's mouth with other data of the virtual model as it pertains to a site map of the mirror location of surgical site, the mirror location being on the contra lateral side of the patient's mouth, allowing the site map of the mirror location to be transposed and overlaid upon the site map of proposed dental implant surgical site; creating from that comparison of virtual model data, a proposed sulcus emergence profile for the implant surgical site; creating a concavity based on the profile; and using the concavity in manufacture of a patient-specific healing abutment, the healing abutment once placed on dental implant at the implant surgical site will promote emergent sulcus development pursuant to the profile.

Another possible embodiment may be a method or process of creating a patient-specific final abutment that meets a proposed sulcus emergence profile for a dental implant surgical site, comprising of the following steps, obtaining data of a specific patient's mouth needed to create a computer-generated virtual model of that patient's mouth; processing said obtained data to create a computer-generated virtual model of the current state of the specific patient's mouth; comparing data of virtual model as it pertains to a site map of a proposed dental implant surgical site of the patient's mouth with other data of the virtual model as it pertains to a site map of the mirror location of surgical site, the mirror location being on the contra lateral side of the patient's mouth, allowing the site map of the mirror location to be transposed and overlaid upon the site map of proposed dental implant surgical site; creating from that comparison of virtual model data, a proposed sulcus emergence profile for the implant surgical site; creating a concavity based on the proposed sulcus emergence profile; and using the concavity in manufacture of a patient-specific final abutment, the final abutment once placed on dental implant at the implant surgical site will support the developed emergent sulcus that has occurred according to profile.

Another possible embodiment may be a method or process of creating a patient-specific crown that meets a proposed sulcus emergence profile for a dental implant surgical site, comprising of the following steps, but not necessarily in the order shown below: obtaining data of a specific patient's mouth needed to create a computer-generated virtual model of that patient's mouth; providing a computer capability with corresponding software needed to process the obtained data into a computer-generated virtual model of the patient's mouth; processing said obtained data to create a computer-generated virtual model of the current state of the specific patient's mouth; comparing data of virtual model as it pertains to a site map of a proposed dental implant surgical site of the patient's mouth with other data of the virtual model as it pertains to a site map of the mirror location of surgical site, the mirror location being on the contra lateral side of the patient's mouth, allowing the site map of the mirror location to be transposed and overlaid upon the site map of proposed dental implant surgical site; creating from that comparison of virtual model data, a proposed sulcus emergence profile for the implant surgical site; creating a concavity based on the sulcus emergence profile; and using the concavity in manufacture of a patient-specific crown, the base of the crown when the crown is placed on a patient specific final abutment secured to a dental implant at the implant surgical site, will support sulcus emergence that has developed pursuant to the profile. Yet another possible embodiment of the invention could be a patient-specific healing abutment that meets a proposed sulcus emergence profile for a dental implant surgical site, comprising of a body made of resilient material and comprised of a top, bottom, and side, the side connecting the top and bottom together, the top and bottom being further continuously connected together by implant channel running through center of the body; wherein at least the side contours of the body are manufactured to meet a proposed sulcus emergence profile, the profile being by created by comparing virtual model data created for the patient's mouth as it pertains to a site map of a proposed dental implant surgical site of the patient's mouth with other virtual model data as it pertains to a site map of the mirror location of surgical site, allowing the site map of the mirror location to be transposed and overlaid upon the site map of proposed dental implant surgical site.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF CERTAIN EMBODIMENTS OF THE PRESENT INVENTION

Figure 1:
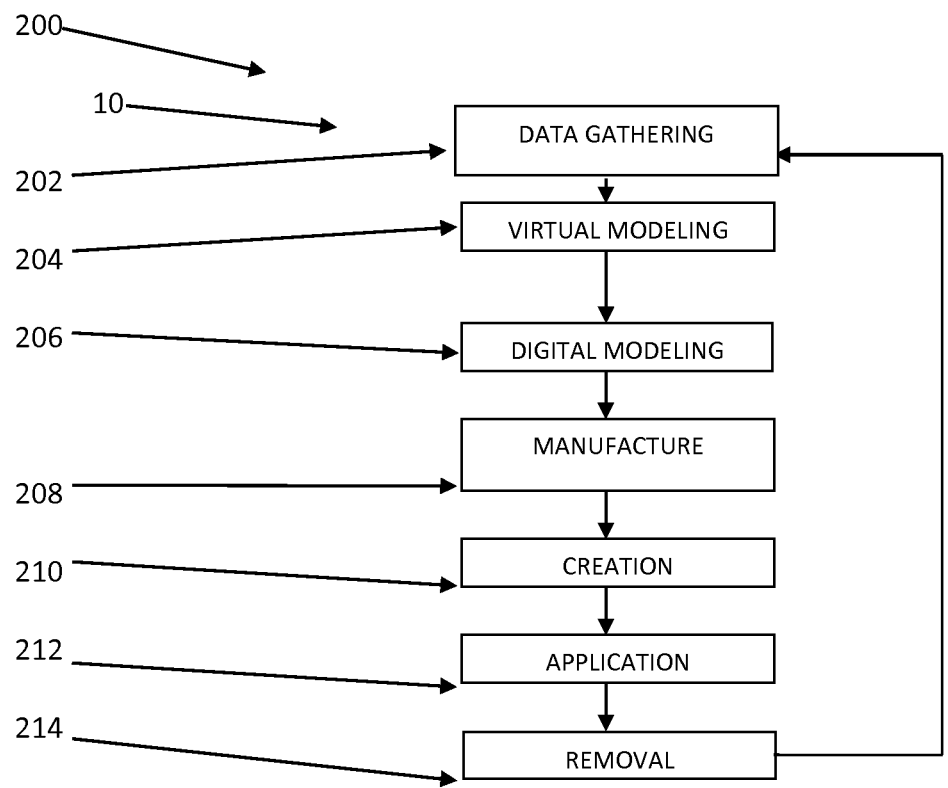
FIG. 1 is substantially a flow chart of one possible embodiment of the method or process of the invention.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

The present invention 10 could comprise of method or process 200 used prior to dental implant surgery (e.g., presurgical) that uses virtual modeling (e.g., virtually created model) of a patient's mouth to further develop a patient-specific, Added Manufacturing or CAD/CAM profile/model of the emergent sulcus at the proposed implant surgical site. This profile could be used to create patient specific apparatus, such a patient-specific healing abutment 20 (shown in FIG. 2), patient-specific final abutment 40 (shown in FIG. 3), and patient specific crown 50 (shown in FIG. 4) which could be used to bring about and then support such a desired emergent sulcus profile. The profile could be used to create a concavity, which is then used in the manufacture of the patient-specific healing abutment 20 as well such as to utilize many of the patient-specific healing abutment dimensions to create a patient-specific crown 50 and a patient-specific final abutment 40. These dental implant components (once attached to a dental implant at an implant surgical site) may bring about the desired sulcus emergence proximate to the surgical implant site (by otherwise generally controlling the augmentation of soft and hard tissue at the surgical implant site) and then further support the emergent sulcus as developed in accordance with the profile.

The process 200 could commence with step 202, data gathering, utilizing means well known to those skilled in the art, such as creation of physical models (e.g., castings/impressions) of a specific patient's mouth may be taken and later could canned to be reduced to digital value. Digital scans of the patient's mouth can also be used to generate data for virtual modeling of the mouth. The patient's mouth could also be scanned with CBCT scan, Optical Scan, and other suitable measuring means. The CBCT scan may provide the hard tissue and root trajectory and its placement, while the Optical Scan/physical models generally establishes tissue values in relation with tooth projection/free gingival margin. After step 202 is substantially completed, the process 200 could proceed to step 204, virtual modeling.

In step 204, virtual modeling, a computing capability in combination with appropriate software modeling programs, as are well known by those skilled in the art, can be utilized to process the gathered data to create a computer supported/generated patient-specific virtual model of the mouth (or at least desired portion[s] of the mouth). Using data of the virtual model as it pertains to a site map of a proposed dental implant surgical site of the patient's mouth and comparing it with other data of the virtual model as it pertains to a site map of the mirror location of surgical site, the mirror location being on the contra lateral side of the patient's mouth, could allow the site map of the mirror location to be transposed and overlaid upon the site map of proposed dental implant surgical site. This comparison of virtual model data could be used to set the orientation and telemetry for the implants and crown as well as set the digital mapping/planning for the foundation for the new prosthetic crown to emerge from the projected development of the emerging sulcus. The virtual model in this manner can be used to establish a proposed sulcus emergence profile denoting how the development of the emergent sulcus could occur at the surgical implant site. This proposed sulcus emergence profile could take into account specific patient's biological anatomical architectures of its specific sulcus anatomy to accurately predict the final outcome of the dental implant surgery in conjunction with the expected sulcus emergence. At the completion of step 204, the process 200 can proceed to step 206, digital modeling of healing abutment.

Step 206, digital modeling of healing abutment, the profile/virtual model data can also be used to create a corresponding concavity (a model of a proposed opening or tooth socket to be occupied by the abutments [e.g., healing/final abutments] and the bottom of the dental crown) that is otherwise surrounded by the emergent sulcus/soft tissue. The proposed patient-specific concavity is then filled in with digital data to create the model of the patient-specific healing abutment. Then the dimensions of the final abutment (especially those dimensions which include contact with the emerging sulcus/soft tissue) may be used to create a virtual model of the final abutment (the final abutment is generally is different from the healing abutment in additionally featuring a post/chimney to which the dental crown could be attached in the final stages of the surgical procedure). In this manner, the base of the final abutment is designed to closely match healing abutment/desired sulcus emergence profile while the chimney is designed to bring and hold the dental crown into the correct position and orientation relative to emerged sulcus when the final abutment replaces the healing abutment at the implant surgical site. At the completion of step 206, the process 200 can proceed to step 208, manufacture of healing abutment.

In step 208, manufacture of healing abutment, the data of the healing abutment's virtual model can be transmitted to manufacture means controlled by computing means/and manufacturing programs (as known to those who are skilled in the art) that can process the virtual modeling data to create the healing abutment that complements the concavity with precision. In this manner, the manufacturing means may create a patient-specific healing abutment that is modeled and designed to bring about the desired profile of the emergent sulcus/soft tissue development when the healing abutment is attached to the dental implant at the implant surgical site.

Figure 2:
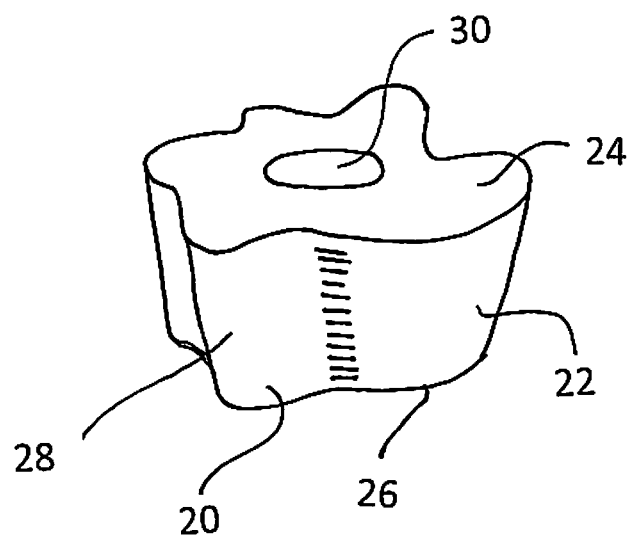
FIG. 2 is substantially showing a patient-specific healing abutment embodiment of the invention.
Figure 3:
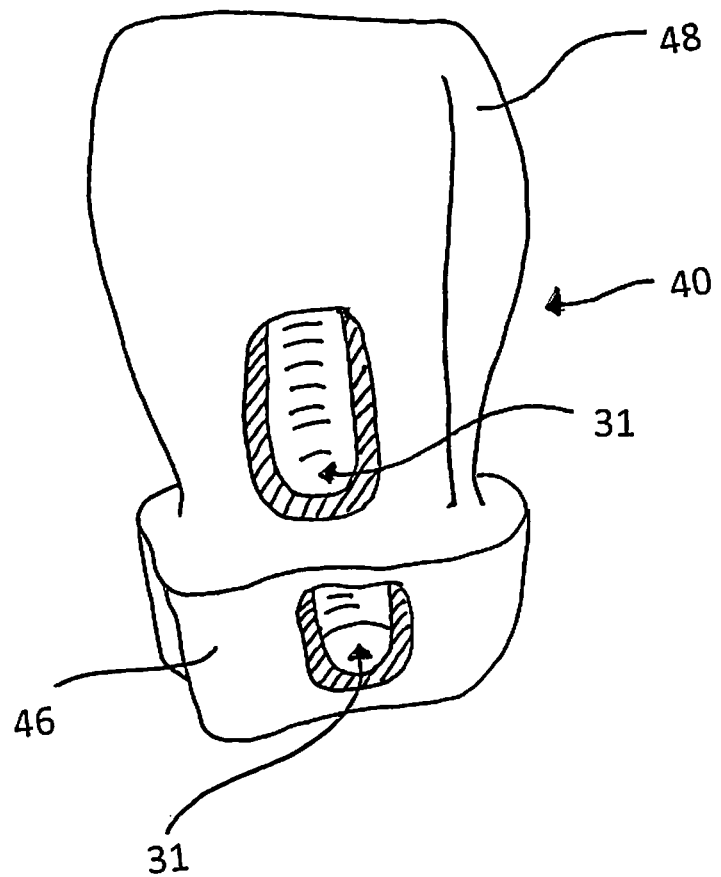
FIG. 3 is substantially patient-specific final abutment embodiment of the invention.

In this manner, the healing abutment 20, as substantially shown in FIG. 2, may comprise of a body 22 made of resilient material and further comprised of a top 24, bottom 26, and side 28, the side 28 connecting the top 24 and bottom 26 together, the top 24 and bottom 26 being further continuously connected together by implant channel 30 running through center of the body 22, wherein at least the contours of side 28 are generally manufactured to meet the proposed sulcus emergence profile. Upon substantial completion of this step 208, the process 200 can subsequently move onto step 210, creation of the final abutment and crown.

In step 210, creation of the final abutment and crown, the data virtual model of the final abutment may be transmitted to computing/manufacture means to create the patient-specific final abutment and patient-specific crown. As substantially shown in FIG. 3, the patient-specific final abutment 40 may be comprised of a base 46 connected to a chimney 48, the base 46 and chimney 48 being traversed by a final abutment implant channel 31 running through the longitudinal center of the final abutment 40. At least the base 46 of the final abutment 40 is substantially designed to designed to closely match the sulcus emergence profile/concavity while its chimney 48 is generally design to bring and hold the dental crown 50 into correct position and orientation relative to emerged sulcus/soft tissue.

Figure 4:
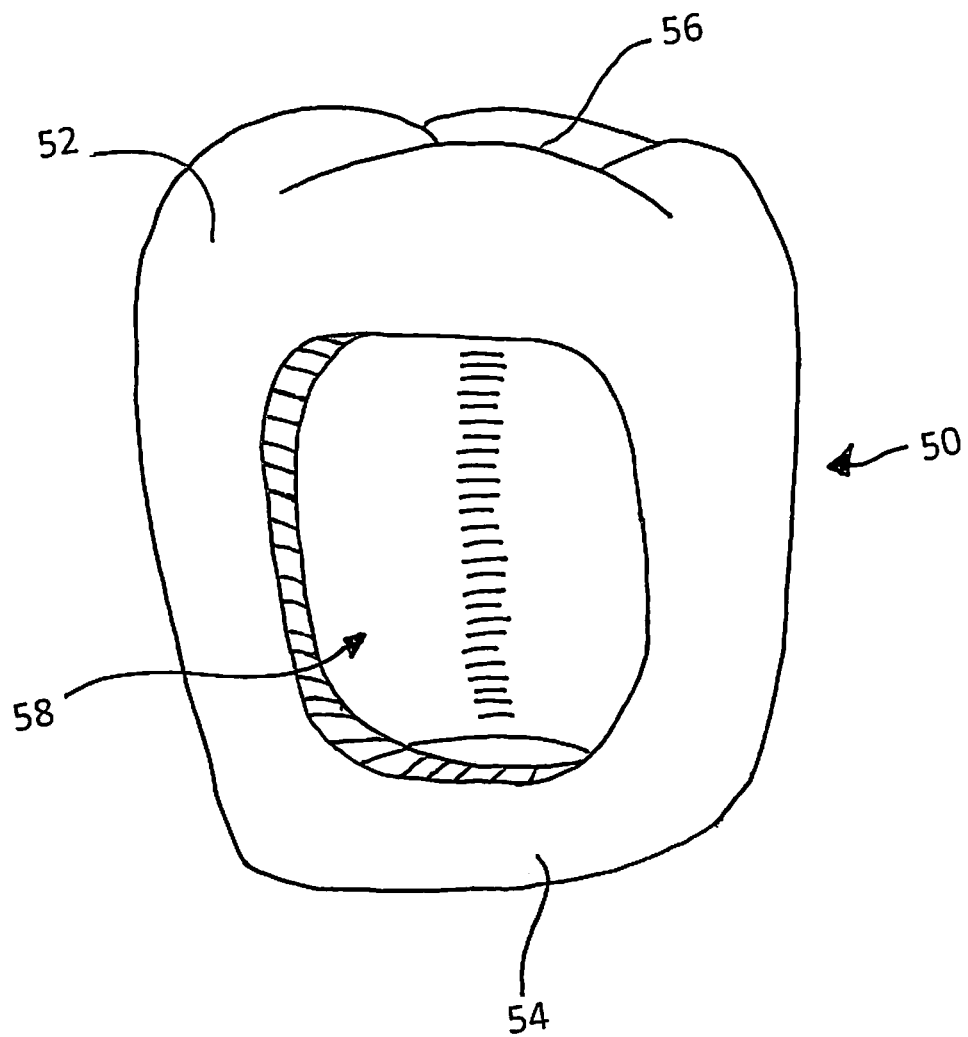
FIG. 4 is substantially patient-specific crown embodiment of the invention.

As substantially shown in FIG. 4, the patient-specific crown 50 may have a crown body 52 comprised of a base 54 connected to tooth portion 56, the base 54 and tooth portion 56 being longitudinally traversed by a chimney channel 58, wherein the base 54 may have its contours constructed to generally match the sulcus emergence profile/concavity.

Upon the substantial completion of step 210, the process 200 can subsequently move onto step 212, application of the healing abutment.

In step 212, application of the healing abutment, the dental implant has been properly secured into the dental surgical site, and the patient-specific healing abutment is reversibly attached (e.g. by fastener) to the top of the dental implant. The top of the healing abutment is generally scalloped formed whose edges would meet the desired profile of emergent free gingival margin (preventing patient interference with the dental surgical site allowing proper/desired sulcus emergence to occur.) The site, if needed, could be further sutured to close any gaps. A retainer, such as the Essix type, can be used, as needed, to present and hold a temporary crown at the dental surgical site. At the substantial completion of step 212, the process 200 can proceed to step 214, removal of the patient-specific healing abutment.

In step 214, removal of healing abutment, a thin, healthy keratinized tissue overgrowth may form over the top of the healing abutment and needs to be removed (e.g., with the use of a laser or scalpel.) The healing abutment may then be unfastened or unscrewed from the dental implant and is removed from the implant surgical site and discarded. At that time, the patient-specific final abutment, whose base generally matches the patient-specific healing abutment dimensions, may be permanently attached to the top of the dental implant. At that time the dental crown may be permanently affixed (e.g., appropriately cemented) to the chimney of the patient-specific final abutment. Upon substantial completion of this step, the process 200 may proceed back to step 202 for use in another dental implant surgical site.

CONCLUSION

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

As substantially shown in this application, the present invention has the ability to use comparing the data of virtual model of a specific-patient's mouth pertaining to the implant surgical site map with other data from that model that pertains to the surgical site's mirror location on the contra-lateral side of the patient's mouth, allowing the site map of the mirror location to be transposed and overlaid upon the site map of proposed dental implant surgical site to create a emerging sulcus profile for the implant surgical site that would be biologically correct and esthetically pleasing when a dental crown is finally fitted to the operation surgical site. The invention may also provide a specifically engineered patient-specific healing abutment, final abutment and crown manufactured using a concavity based on the profile. The healing abutment's placement at a implant surgical site will generally assist the promotion of desired sulcus emergence according to the profile while the placement of patient specific final abutment and crown could have the ability to generally support the emergent sulcus as it had developed according to profile.

What is claimed is:
1. A method of creating a proposed sulcus emergence profile for a dental implant surgical site, comprising the following steps, but not necessarily in the order shown below:
    (A) obtaining data of a specific patient's mouth needed to create a computer-generated virtual model of the specific patient's mouth;
    (B) processing said obtained data to create the computer-generated virtual model of the specific patient's mouth;
    (C) comparing virtual model data as it pertains to a site map of a proposed dental implant surgical site of the patient's mouth with other virtual model data as that pertains to a site map of the mirror location of the proposed dental implant surgical site, the mirror location being on the contra lateral side of the patient's mouth from the proposed dental implant surgical site, allowing the site map of the mirror location to be transposed and overlaid upon the site map of the proposed dental implant surgical site;
    (D) creating from that comparison of virtual model data, a proposed sulcus emergence profile for the proposed implant surgical site;
    (E) creating a concavity based on the proposed sulcus emergence profile;
    (F) using the concavity in a manufacture of a patient-specific healing abutment that will support the sulcus emergence as developed pursuant to the proposed sulcus emergence profile, the patient-specific healing abutment further lacking a chimney of a patient-specific final abutment.

2. The method of claim 1 further comprising a step of using the concavity in a manufacture of the patient-specific final abutment that will support the sulcus emergence that has developed pursuant to the proposed sulcus emergence profile.

3. The method of claim 2 further comprising a step of promoting actual sulcus emergence according to the proposed sulcus emergence profile by reversibly attaching the patient-specific healing abutment to a dental implant inserted in the proposed implant surgical site.

4. The method of claim 3 further comprising a step of removing the patient-specific healing abutment from the dental implant when a sulcus emergence substantially conforms to the proposed sulcus emergence profile.

5. The method of claim 4 further comprising a step of securing the patient-specific final abutment to the dental implant when the sulcus emergence substantially conforms to the proposed sulcus emergence profile.

6. The method of claim 1 further comprising a step of using the concavity to create a crown whose base contours substantially conform to the proposed sulcus emergence profile.

7. A method of creating a patient-specific healing abutment that meets a proposed sulcus emergence profile for a dental implant surgical site, comprising the following steps, but not necessarily in the order shown below:
 (A) obtaining data of a specific patient's mouth needed to create a computer-generated virtual model of the specific patient's mouth;
 (B) processing said obtained data to create the computer-generated virtual model of a current state of the specific patient's mouth;
 (C) comparing data of the computer-generated virtual model of the current state as it pertains to a site map of a proposed dental implant surgical site of the specific patient's mouth with other data of the virtual model as that pertains to a site map of the mirror location of the proposed dental implant surgical site, the mirror location being on the contra lateral side of the specific patient's mouth from the proposed dental implant surgical site, allowing the site map of the mirror location to be transposed and overlaid upon the site map of the proposed dental implant surgical site;
 (D) creating from that comparison of virtual model data, a proposed sulcus emergence profile for the implant surgical site;
 (E) creating a concavity based on the proposed sulcus emergence profile; and
 (F) using the concavity in manufacture of a patient-specific healing abutment, the created patient-specific healing abutment being capable of promoting sulcus emergence pursuant to the proposed sulcus emergence profile, the created patient-specific healing abutment further lacking a chimney of a patient-specific final abutment.

8. The method of claim 7 further comprising a step of using the concavity in a computer-created manufacture of a patient-specific final abutment whose contours conform to the proposed sulcus emergence profile.

9. The method of claim 8 further comprising a step of supporting the sulcus emergence that has occurred according to the proposed sulcus emergence profile by attaching the patient-specific final abutment to a dental implant at the implant surgical site.

10. The method of claim 7 further comprising a step of securing the patient-specific healing abutment to a dental implant at the implant surgical site to promote the sulcus emergence pursuant to the proposed sulcus emergence profile.

11. The method of claim 10 further comprising a step of replacing the patient-specific healing abutment at the dental implant with a patient-specific final abutment manufactured to conform to the proposed sulcus emergence profile when the sulcus emergence has occurred according to the proposed sulcus emergence profile.

12. A method of creating a patient-specific abutments that meet a proposed sulcus emergence profile for a dental implant surgical site, comprising the following steps, but not necessarily in the order shown below:
 (A) obtaining data of a specific patient's mouth needed to create a computer-generated virtual model of the specific patient's mouth;
 (B) processing said obtained data to create the computer-generated virtual model of a current state of the specific patient's mouth;
 (C) comparing data of the computer-generated virtual model as it pertains to a site map of a proposed dental implant surgical site of the specific patient's mouth with other data of the computer-generated virtual model as that pertains to a site map of the mirror location of the proposed dental implant surgical site, the mirror location being on the contra lateral side of the specific patient's mouth of the proposed dental implant surgical site, allowing the site map of the mirror location to be transposed and overlaid upon the site map of the proposed dental implant surgical site;
 (D) creating from that comparison of virtual model data, a proposed sulcus emergence profile for the proposed dental implant surgical site;
 (E) creating a concavity based on the proposed sulcus emergence profile; and
 (F) using the concavity in manufacture of a patient-specific healing abutment as well as patient-specific final abutment, the patient-specific final abutment being capable of supporting a sulcus emergence that has occurred in accordance with the proposed sulcus emergence profile, the patient-specific final abutment further featuring a chimney not found in the patient-specific healing abutment.

13. The method of claim 12 further comprising a step of promoting the development of the sulcus emergence in accordance with the proposed sulcus emergence profile by securing the patient-specific healing abutment to a dental implant anchored at the proposed dental implant surgical site.

14. The method of claim 13 further comprising a step of removing the patient-specific healing abutment from the dental implant when the sulcus emergence substantially meets the proposed sulcus emergence profile.

15. The method of claim 12 further comprising a step of replacing a patient-specific healing abutment with the patient-specific final abutment when the emergent sulcus substantially meets the proposed sulcus emergence profile.

16. The method of claim 12 further comprising a step of supporting the sulcus emergence that has substantially met the proposed sulcus emergence profile by attaching the patient-specific final abutment to a dental implant.

17. A method of creating a patient-specific crown that meets a proposed sulcus emergence profile for a dental implant surgical site, comprising the following steps, but not necessarily in the order shown below:
 (A) obtaining data of a specific patient's mouth needed to create a computer-generated virtual model of a current state of the specific patient's mouth;
 (B) processing said obtained data to create the computer-generated virtual model of the current state of the specific patient's mouth;
 (C) comparing data of the computer-generated virtual model as it pertains to a site map of a proposed dental implant surgical site of the patient's mouth with other data of the virtual model as that pertains to a site map of a mirror location of the proposed dental implant surgical site, the mirror location being on the contra lateral side of the patient's mouth of the proposed dental implant surgical site;

(D) transporting and overlaying the site map of the mirror location upon the site map of the proposed dental implant surgical site;

(E) creating from that comparison of virtual model data, a proposed sulcus emergence profile for the proposed dental implant surgical site;

(E) creating a concavity based on the proposed sulcus emergence profile; and (F) using the concavity in manufacture of a patient-specific crown, the patient-specific crown's base being capable of supporting a sulcus emergence that has developed in accordance with the proposed sulcus emergence profile;

(G) a step of further using the concavity in a computer-created manufacture of a patient-specific healing abutment, the patient-specific healing abutment lacking a chimney as found on a patient-specific final abutment, the patient-specific healing abutment once placed on a dental implant at the implant surgical site will develop the sulcus emergence according to the proposed sulcus emergence profile.

18. The method of claim 17 further comprising step of using the concavity in a computer-created manufacture of a patient-specific final abutment, the resulting patient-specific final abutment conforms to the proposed sulcus emergence profile.

19. The method of claim 18 further comprising a step of applying the patient-specific healing abutment to the dental implant at the implant surgical site to develop the sulcus emergence in accordance with the proposed sulcus emergence profile.

20. The method of claim 19 further comprising a step of replacing the patient-specific healing abutment with the patient-specific final abutment when the sulcus emergence has developed in accordance with the proposed sulcus emergence profile, then attaching the crown to the patient-specific final abutment, the patient-specific final abutment and crown so combined supports the sulcus emergence as developed in accordance with the proposed sulcus emergence profile.

21. The method of claim 17 further comprising a step of using the concavity in a computer-created manufacture of a patient-specific healing abutment and a patient specific final abutment, using the patient-specific healing abutment to develop the sulcus emergence in accordance with the proposed sulcus emergence profile, and using the patient-specific final abutment to later support the sulcus emergence that has developed in accordance with the proposed sulcus emergence profile.

* * * * *